(12) United States Patent
Suzuki et al.

(10) Patent No.: US 8,288,604 B2
(45) Date of Patent: Oct. 16, 2012

(54) METHOD OF RAPID METHYLATION, KIT FOR PREPARING PET TRACER AND METHOD OF PRODUCING PET TRACER

(75) Inventors: Masaaki Suzuki, Gifu (JP); Hisashi Doi, Wakou (JP); Hideo Tsukada, Hamamatsu (JP)

(73) Assignees: Gifu University, Gifu (JP); Riken, Saitama (JP); Hamamatsu Photonics K.K., Shizuoka (JP)

( * ) Notice: Subject to any disclaimer, the term of this patent is extended or adjusted under 35 U.S.C. 154(b) by 619 days.

(21) Appl. No.: 12/438,711

(22) PCT Filed: Aug. 24, 2007

(86) PCT No.: PCT/JP2007/066411
§ 371 (c)(1),
(2), (4) Date: Feb. 24, 2009

(87) PCT Pub. No.: WO2008/023780
PCT Pub. Date: Feb. 28, 2008

(65) Prior Publication Data
US 2010/0249477 A1  Sep. 30, 2010

(30) Foreign Application Priority Data

Aug. 25, 2006 (JP) .................. 2006-229169

(51) Int. Cl.
*C07C 2/60* (2006.01)
*C07C 2/68* (2006.01)

(52) U.S. Cl. .......... 585/446; 585/24; 585/400; 585/457; 585/469; 585/471; 585/500; 585/638; 585/641; 585/643

(58) Field of Classification Search .................. 585/400, 585/470, 471, 469, 24, 446, 457, 500, 638, 585/641, 643
See application file for complete search history.

(56) References Cited

FOREIGN PATENT DOCUMENTS

| JP | H07-165630 A | 6/1995 |
|----|--------------|--------|
| JP | H11-332589 A | 12/1999 |
| JP | 2001-240563 A | 9/2001 |
| JP | 2002-308613 A | 10/2002 |
| JP | 2004-536082 A | 12/2002 |

(Continued)

OTHER PUBLICATIONS

Hostetler, et al., "An Improved Synthesis of Substituted [11C]Toluenes via Suzuki Coupling with [11C] Methyl Iodide" in J. Label Compd. Radiopharm., 2005, 48(9), 629-634.*

(Continued)

*Primary Examiner* — In Suk Bullock
*Assistant Examiner* — Bradley Etherton
(74) *Attorney, Agent, or Firm* — Quarles & Brady LLP; Gavin J. Milczarek-Desai

(57) ABSTRACT

A method of rapid methylation of an aromatic compound or an alkenyl compound, which is capable of obtaining an aromatic compound or an alkenyl compound labeled with a methyl group or a fluoromethyl group under a mild condition rapidly in high yield using an organic boron compound whose toxicity is not so high as a substrate. A kit for preparing a PET tracer and a method of producing a PET tracer can be practiced using the rapid methylation method. In an aprotic polar solvent, methyl iodide or X—CH2F (wherein X is a functional group which can be easily released as an anion), and an organic boron compound in which an aromatic ring or an alkenyl group is attached to boron are subjected to crosscoupling in the presence of a palladium(0) complex, a phosphine ligand, and a base.

36 Claims, 1 Drawing Sheet

FOREIGN PATENT DOCUMENTS

| | | |
|---|---|---|
| JP | 2005-502617 A | 1/2003 |
| JP | 2006-509046 A | 6/2004 |
| JP | 2005-053803 A | 3/2005 |
| WO | WO 2007/046258 A1 | 4/2007 |

OTHER PUBLICATIONS

Miyaura, et al., "Palladium Catalyzed Cross-Coupling Reactions of Organoboron Compounds" in Chem. Rev., 1995, 95, 2457-2483—1995, no month.*

Miyaura, "Metal Catalyzed Cross-Coupling Reactions of Organoboron Compounds with Organic Halides" in Metal Catalyzed Cross- Coupling Reactions, 2nd ed., Wiley-VCH,—Sep. 2004.*

Crabtree, Chapter 4. Carbonyls, Phosphine Complexes, and Ligand Substitution Reactions in the Organometallic Chemistry of the Transition Metals, 4th ed., John Wiley and Sons—2005, no month.*

Frisch, et al ("Catalysts for Cross-Coupling Reactions with Non-Activated Alkyl Halides" in Angew. Chem. Int. Ed., 2005, 44, 674-688—2005, no month.*

Suzuki, et al., Rapid Coupling of Methyl Iodide with Aryltributylstannanes Mediated by Palladium(0) Complexes: A General Protocol for the Synthesis of 11CH3-Labeled PET Tracers; Chem.Eur.J. 1997, 3, No. 12, pp. 2039-2042—1997.

Hostetler, et al., "An Improved Synthesis of Substituted [11C]toluenes via Suzuki Coupling with [11C]methyl Iodide", Journal of Labelled Compounds and Radiopharmaceuticals, 2005; 48 pp. 629-634—Jun. 2005.

Hostetler, et al., "An Improved Synthesis of Substituted [11C]toluenes via Suzuki Coupling with [11C]methyl Iodide", Chemical Abstracts, vol. 144, abs. No. 350336—Sep. 2005.

* cited by examiner

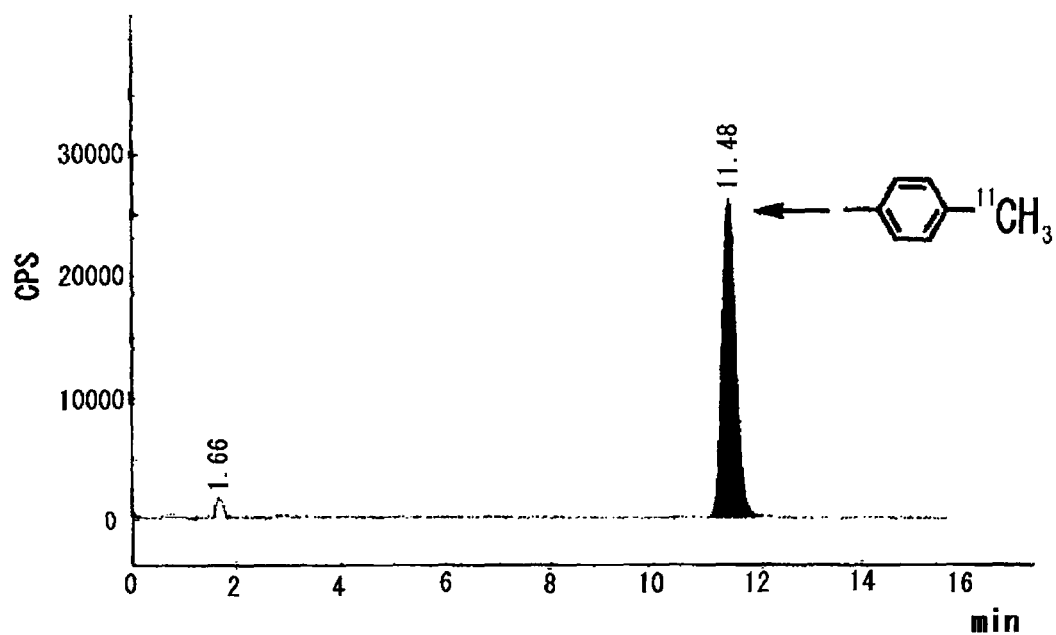

METHOD OF RAPID METHYLATION, KIT FOR PREPARING PET TRACER AND METHOD OF PRODUCING PET TRACER

TECHNICAL FIELD

The present invention relates to a method of rapid methylation for carrying out methylation or fluoromethylation of an aromatic compound or an alkenyl compound for a short time. The present invention can be suitably used for synthesizing a radioactive tracer that plays an important role in positron emission tomography (hereinafter, referred to as "PET").

BACKGROUND ART

In a PET method, a labeled compound labeled with a short-lived radionuclide that emits positron (hereinafter, referred to as a "tracer") is administered into a living body, γ rays generated by this tracer are measured by using a PET camera (a detector including a gamma-ray scintillator and a photomultiplier), and the distribution thereof in the body is imaged by using a computer. This PET method is used in identification of a site of a tumor such as a cancer cell as an examination of nuclear medicine; a diagnosis of Alzheimer disease, brain infarction, and the like; a diagnosis of a mental disorder such as depression; an evaluation of treatment; and an evaluation of pharmacokinetics and drug efficacy.

As a short-lived radionuclide used in a PET method, $^{11}C$ and $^{18}F$ are well used. Since a $^{11}C$-labeled tracer uses a carbon atom existing in all organic compounds, it is applicable in an extremely wide range and becomes an ideal radionuclide. Furthermore, a method of preparing a compound such as $^{11}CH_3I$, $^{11}CO$ or $^{11}CO_2$ serving as a precursor for synthesizing the $^{11}C$-labeled tracer is well established. Therefore, purified precursors can be stably obtained. Therefore, it can be said that the $^{11}C$-labeled tracer is an excellent tracer used in the PET method.

However, since the half-life of $^{11}C$ is only about 20 minutes, it is said that labeling reaction with $^{11}C$ including synthesis, purification and administration to a living body must be carried out within 40 minutes (within twice of the half time). Therefore, various methods for synthesizing PET tracers by using $^{11}C$ for a short time have been considered.

In order to synthesize a PET tracer, hitherto, a methyl group labeled with $^{11}C$ has been tried to be introduced into a heteroatom such as O, N, S or the like. In this method, however, since $^{11}C$ is bonded to heteroatoms such as O, N, S and the like that are unstable to metabolism, a $^{11}C$ methyl group may be released by metabolism before it reaches to a target organ in a living body. Therefore, it may not be possible to carry out a diagnosis and to evaluate treatment accurately.

In contrast, when a $^{11}C$-labeled methyl group is directly bonded to a carbon atom of an organic compound, the following advantages can be obtained.

Firstly, since a methyl group is a three-dimensionally smallest and non-polar functional group, the effect of the methyl group on the bioactivity of the parent compound can be minimized after introduction.

Secondly, since a $^{11}C$-labeled tracer has a short half-life of about 20 minutes, it is possible to carry out a large number of trials and clinical tests in a day. Furthermore, it is not necessary to pay a particular attention to processing of radio-labeled byproducts generated after a synthesis reaction, and the like.

Thirdly, a C-methylated product shows higher stability to metabolism as compared with an O-methylated product or an N-methylated product, and in the C-methylated product, $^{11}C$ methyl can be introduced into parent nuclei of carbon of an important compound such as a metabolism-related compound or antimetabolite. As mentioned above, when a metabolism-related compound, antimetabolite or the like in which a parent nuclei structure of carbon is labeled with $^{11}C$ methyl in a stable form is used, it is possible to more accurately evaluate diagnosis and treatment of various diseases.

A method of synthesizing a $^{11}C$-labeled compound is described in the following documents.

That is to say, patent document 1 discloses a method of producing $^{11}C$-labeled methyl iodide. The method includes the step of mixing carbon dioxide and hydrogen under pressure so as to form a first mixture, a step of passing the first mixture through catalyst so as to generate methanol, and a step of passing the methanol through an iodination reagent so as to be formed into methyl iodide.

Furthermore, patent document 2 discloses a method of synthesizing $^{11}C$-L-methionine by converting $^{11}C$ methane thiol into $^{11}C$-L-methionine via an enzyme reaction of γ-cyano-α-aminobutyric acid synthase.

Furthermore, patent document 3 discloses a method of synthesizing $^{11}C$-labeled phosgene from $^{11}C$-labeled carbon tetrachloride by using iron oxide.

Furthermore, patent document 4 discloses a method of synthesizing a $^{11}C$-labeled halogenated methyl in which $LiAlH_4$ dissolved in an organic solvent is introduced into a thin tube; an inert gas is allowed to pass through the solution so as to evaporate the solvent and a thin film of the remaining $LiAlH_4$ is formed on a internal surface of the thin tube; then $^{11}CO_2$ gas is introduced so as to be reacted with the remaining $LiAlH_4$; and further a halogenated hydroacid or halogenated hydrogen gas is introduced so as to produce $^{11}CH_3X$ (wherein X represents a halogen atom) in the thin tube.

Furthermore, patent document 5 discloses a method of obtaining fluorine-labeled DOPA by a solid phase method in order to rapidly synthesize a PET tracer monitoring dopamine metabolism of the cerebrum by using $^{18}F$ having a half life of 110 minutes. That is to say, in this method, in order to shorten the purification process of the synthesized labeled compound, $^{18}F$-labeled 6-L-fluoro DOPA is obtained by adding fluorine to DOPA protected by dimethyl tin and linked to a solid support via a linker.

The methods of preparing a PET tracer using $^{11}C$ described in the above-mentioned patent documents have still required a long time for synthesis for preparing the PET tracer and have not provide satisfactory yield and purity. Therefore, these methods are not sufficient for carrying out diagnosis or study of pharmacokinetics reliably. Therefore, a method of introducing $^{11}C$ radio nucleus has been demanded which is a higher-speed reaction and has a higher yield.

Under such circumstances, the present inventors have developed a high-speed methylation method of subjecting methyl iodide and an organic tin compound to a Stille-coupling reaction and received much attention (non-patent document 1). This method has enabled a cross-coupling between carbon of an aromatic ring and $SP^3$ carbon, which has been conventionally thought to be difficult. For example, when methyl iodide, an excessive amount of tributylphenylstannane, tri-o-tolylphosphine and unsaturated palladium are reacted with each other in the presence of a copper salt and potassium carbonate in a DMF solvent at 60° C. for 5 minutes, methylation proceeds in a yield of 90% or more. Many drugs and drug candidate compounds have an aromatic ring or an alkenyl group in its basic skeleton. Since this method enabling a cross-coupling between carbon of the aromatic ring and $SP^3$ carbon permits introduction of a $^{11}C$-labeled methyl group into the aromatic ring, the kinetics of these drugs and drug candidate compounds in a living body can be clarified thereby. The present inventors have actually applied this method to a prostaglandin derivative tracer and succeeded in imaging a prostaglandin receptor in the human brain. Thus, the usefulness thereof has already been verified.

Furthermore, non-patent document 2 reports the synthesis of a $^{11}$C-labeled PET tracer using an organic boron compound. This method is classified in Suzuki-Miyaura reaction in which a compound wherein a benzene ring is bonded to a boron atom and $^{11}$C-labeled methyl iodide are subjected to cross-coupling while heating in a DMF solvent in the presence of Pd (dppf) Cl$_2$ and potassium phosphate in a microwave so as to obtain a $^{11}$C-labeled toluene derivative.

On the other hand, $^{18}$F has a half life (110 minutes) that is five times or longer than that of $^{11}$C (about 20 minutes) and has an advantageous that it is possible to extend the time for preparing a PET tracer and a time for carrying out PET diagnosis. Therefore, a technology for cross-coupling between an aromatic compound or an alkenyl compound and an $^{18}$F-labeled fluoromethyl group has been demanded. However, a method of modifying an aromatic compound or an alkenyl compound with an $^{18}$F-labeled fluoromethyl group rapidly and in a high yield has not been known.

[Patent document 1] JP-H07-165630 A
[Patent document 2] JP-H11-332589 A
[Patent document 3] JP-2002-308615 A
[Patent document 4] JP-2005-53803 A
[Patent document 5] JP-2005-502617 A
[Non-patent document 1] Chem. Eur. J. 1997, 3 (12), 2039-2042
[Non-patent document 2] Journal of Labelled Compounds and Radiopharmaceuticals 48, 629-634 (2005)

DISCLOSURE OF THE INVENTION

Problems to be Solved by the Invention

However, the method of rapid methylation described in the above-mentioned non-patent document 1 has a problem that a highly toxic organic tin (compound is used as a substrate. Furthermore, the method of rapid methylation described in non-patent document 2 uses a less toxic organic boron compound is used as a substrate, but it requires a microwave apparatus and also requires stringent conditions.

The present invention has been made from the viewpoint of the above-mentioned situations. An object of the present invention is to provide a method of rapid methylation of an aromatic compound or an alkenyl compound, which is capable of obtaining an aromatic compound or an alkenyl compound labeled with $^{11}$C-labeled methyl group or $^{18}$F-labeled fluoromethyl group in a mild conditions rapidly and in a high yield by using a less toxic organic boron compound as a substrate; a kit for preparing a PET tracer used therefor; and a method of producing a PET tracer using the same.

Means to Solve the Problems

In order to solve the above-mentioned problems, the present inventors have further keenly investigated whether or not a method of rapid methylation for subjecting methyl iodide and an organic tin compound to coupling reaction described in non-patent document 1 can be applied to an organic boron compound. As a result, the present inventors have found breakthrough novel reaction conditions capable of solving the above-mentioned problems and have reached the present invention.

That is to say, the first aspect of a method of rapid methylation of an aromatic compound or an alkenyl compound of the present invention comprises;

cross coupling methyl iodide or X—CH$_2$F, wherein X is a functional group that can be easily released as an anion, and an organic boron compound in which an aromatic ring or an alkenyl group is bonded to boron in an aprotic polar solvent in the presence of a palladium (0) complex, a phosphine ligand and a base.

Herein, the aromatic compound also includes a heterocyclic aromatic compound in addition to benzene and its derivatives; the aromatic ring includes also a heterocyclic aromatic ring in addition to a benzene ring.

According to the test results by the inventors, when the method of rapid methylation of an aromatic compound or an alkenyl compound of the present invention is used, a coupling reaction between SP$^2$—SP$^3$ carbon atoms proceeds smoothly, and a compound in which a methyl group or a fluoromethyl group is bonded to an aromatic compound or an alkenyl compound can be obtained rapidly and in a high yield. This reaction is estimated to proceed by the following mechanism.

That is to say, firstly, a three-dimensionally bulky phosphine ligand is coordinated to a palladium complex having a valence of zero (hereinafter, referred to as "palladium (0) complex") in an unsaturated manner, thus creating an active reaction field. Furthermore, the palladium complex in which this phosphine ligand is coordinated and methyl iodide or X—CH$_2$F are reacted with each other so as to form a palladium complex having a valence of two in which the phosphine ligand is coordinated to CH$_3$PdI or FCH$_2$PdX.

On the other hand, a boron ate complex is formed in which a base is coordinated to boron of an organic boron compound in which an aromatic ring or an alkenyl group is bonded to the boron to heighten the polarity between the boron and the carbon.

Then, the above-mentioned palladium complex valence of two to which the phosphine ligand is coordinated and the boron ate complex undergo a transmetalation and furthermore, I$^-$ or X$^-$ anion is released, and thus a more stable boron ate complex is formed.

Finally, a reductive release reaction occurs, and a compound in which a methyl group or a fluoromethyl group is bonded to an aromatic compound or an alkenyl compound is obtained.

Since the reaction is carried out in an aprotic polar solvent such as DMF, an aprotic polar solvent is coordinated to a vacant orbit of a palladium atom of the palladium complex generated in the middle of the reaction, so that the instability thereof is reduced and a side reaction such as decomposition can be minimized.

Therefore, according to the first aspect of the method of rapid methylation of an aromatic compound or an alkenyl compound in the present invention, it is possible to obtain an aromatic compound or an alkenyl compound labeled with a $^{11}$C-labeled methyl group or an $^{18}$F-labeled fluoromethyl group in a mild condition rapidly and in a high yield by using not so highly toxic organic boron compound as a substrate.

In the second aspect of the present invention, the methyl iodide is labeled with a carbon isotope other than $^{12}$C and/or a hydrogen isotope other than $^1$H. Thus, since an aromatic compound or an alkenyl compound that is labeled with a carbon isotope other than $^{12}$C or a hydrogen isotope other than $^1$H can be obtained, it is possible to effectively use these compounds as a molecular probe for studying metabolism or research and development of drugs as a molecule probe. An example of the carbon isotope other than $^{12}$C can include $^{11}$C, $^{13}$C, $^{14}$C and the like, and an example of the hydrogen isotope other than $^1$H can include heavy hydrogen and the like. In particular, $^{11}$C is useful as a PET tracer.

According to the third aspect of the present invention, X—CH$_2$F is labeled with $^{18}$F. Since $^{18}$F has a long half-life of 110 minutes, it is advantageous that time for preparing a PET tracer or time for carrying out PET diagnosis can be extended. Furthermore, time for converting a PET tracer labeled with CH$_2$$^{18}$F into a further compound occurs. Therefore, when a PET tracer labeled with CH$_2$$^{18}$F is bonded to materials such as enzyme, antigen, antibody, and the like, by a click reaction and PET photographing is carried out, distribution of an enzyme protein or a receptor of antigen or distribution of an antibody, which is labeled by a click reaction, is imaged. Thus, elucidation of the function of enzyme, antigen-antibody reaction and the like, which are an important tool for biochemical studying, can be provided.

From the above-mentioned description of the reaction mechanism, X in X—CH$_2$F may be any substituents as long as anion release can be carried out easily. The present inventors have found that when X is I, the above-mentioned reaction proceeds smoothly. Therefore, in the fourth aspect of the present invention, X is made to be I. Also in the case where X is Br, a tosyl group, a mesyl group, a triflate group, and the like, instead of I, it is naturally anticipated from the common knowledge of organic chemistry that the same reaction proceeds smoothly.

According to the fifth aspect of the present invention, the organic boron compound in which an aromatic ring or an alkenyl group is bonded to boron is an aromatic boronic acid ester or an alkenyl boronic acid ester. The present inventors have confirmed that the addition of a methyl group and a fluoromethyl group to an aromatic compound or an alkenyl compound is achieved rapidly and in a high yield by using an aromatic boronic acid ester or an alkenyl boronic acid ester as the organic boron compound.

It is preferable that the aromatic boronic acid ester or the alkenyl boronic acid ester is pinacol ester. Thus, in the reductive release reaction in the final stage of the method of rapid methylation of the aromatic compound or the alkenyl compound of the present invention, a pinacol borate having a high polarity is generated. Thus, when a target material is generated and separated from the reaction solution by a reverse-phase liquid chromatography, and the like, the retention time of a pinacol borate having a high polarity becomes shorter than the retention time of the targeted material or a large amount of the remaining starting substrate. Therefore, it is possible to carry out separation more completely.

According to the sixth aspect of the present invention, the base is a carbonate that may include water and/or a phosphate that may include water. The present inventors have confirmed that the addition of a methyl group and a fluoromethyl group to an aromatic compound or an alkenyl compound is reliably achieved rapidly and in a high yield by using such a base.

According to the seventh aspect of the present invention, the phosphine ligand is tri-o-tolylphosphine or (di-t-butyl) methylphosphine. The present inventors have confirmed that a methyl alkene can be obtained more rapidly and in a higher yield by using such a phosphine ligand. This is thought to be because bulkiness of tri-o-tolyl phosphine or (di-tert-butyl) methylphosphine creates a highly active reaction field. Furthermore, tri-o-tolylphosphine has an advantage that it is more stable as a crystalline compound in the air and is more easily treated as compared with (di-tert-butyl)methylphosphine.

According to the eighth aspect of the present invention, the palladium (0) complex is tris(dibenzylideneacetone) dipalladium (0). The present inventors have confirmed that methylation proceeds rapidly and in a high yield when this palladium (0) complex is used. It is particularly preferable that the palladium (0) complex is tris(dibenzylideneacetone) dipalladium (0) and the phosphine ligand is tri-o-tolylphosphine or (di-t-butyl)methylphosphine. Therefore, in the ninth aspect of the present invention, the palladium (0) complex is tris (dibenzylideneacetone) dipalladium (0), and the phosphine ligand is tri-o-tolylphosphine or (di-t-butyl)methylphosphine.

According to the tenth aspect of the present invention, the organic boron compound in which an aromatic ring or an alkenyl group is bonded to boron, a palladium (0) complex, a phosphine ligand and a base are used in not less than an equivalent amount with respect to the methyl iodide or X—CH$_2$F. According to the test results by the present inventors, it has been confirmed that when the organic boron compound in which an aromatic ring or an alkenyl group is bonded to boron, a palladium (0) complex, a phosphine ligand and a base are used in not less than an equivalent amount with respect to X—CH$_2$F, an intended compound can be obtained in a high yield.

In particular, it is preferable that the amount of the phosphine ligand is not less than four times the palladium (0) complex in a mole ratio. Therefore, in the eleventh aspect of the present invention, the amount of the phosphine ligand is not less than four times the palladium (0) complex in a mole ratio.

In the method of rapid methylation in accordance with the present invention, in the organic boron compound as a substrate in which an aromatic ring is bonded to boron, the aromatic ring is not particularly limited and may be an aromatic ring having heterocycle. Therefore, in the 12th aspect of the present invention, the aromatic ring includes heterocycle. According to the test results by the present inventors, when the aromatic ring is not only a heterocycle such as a thiophenyl group or a furanyl group but also a strongly basic heterocycle such as a pyridyl group or an isoquinolinyl group, the methylation can be carried out in a high yield. The method of methylation can be generally applied to a wide range of aromatic rings. An example of the aromatic ring having such a heterocycle may include a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzoisooxazole ring, a benzoisothiazole ring, a benzimidazole ring, a pyridine ring, pyrazine ring, a pyridazine ring, a pyrimidine ring, a triazine ring, a quinoline ring, an isoquinoline ring, a sinoline ring, a quinoxaline ring, a perimidine ring, a quinazoline ring, and the like. As a drug, a large number of compounds having a heterocycle as a basic skeleton are known. The method of rapid methylation capable of producing such compounds is an extremely useful method of producing a PET tracer for studying drugs.

Also, it is possible to carry out the methylation or fluoromethylation of an aromatic compound or an alkenyl compound by preparing a kit in which reagents to be used for the method of rapid methylation of an aromatic compound or an alkenyl compound of the present invention are previously mixed, followed by adding an aprotic polar solvent thereto, and further introducing methyl iodide or X—CH$_2$F thereinto. That is to say, the kit for preparing a PET tracer of the present invention is characterized by including an organic boron compound in which an aromatic ring or an alkenyl group is bonded to boron, a palladium (0) complex, a phosphine ligand and a base. When such a kit for preparing a PET tracer is prepared, only by adding an aprotic polar solvent and introducing $^{11}$C-labeled methyl iodide or a $^{11}$C-labeled X—CH$_2$F, a PET tracer can be synthesized in an extremely simple manner.

It is preferable that the kit further includes a column for separating an intended compound from the solution after completion of the reaction. Thus, it is not necessary to additionally prepare a column, and thereby a more convenient kit for preparing a PET tracer can be obtained. As a column, a HPLC separation column is preferable. It is more preferable that a reverse-phase column suitable for separating a polarity compound is used. It is the most preferable that a kit is made by combining a reverse-phase precolumn and a reverse-phase silica gel column for purification.

By using a kit which contains other reagents measured at the ratio capable of producing the highest yield with respect to one equivalent of the methyl iodide labeled with an extremely small amount of $^{11}$C and the X—CH$_2$F labeled with an extremely small amount of $^{11}$C, measuring is not needed when it is used. By only mixing and reacting in situ, an intended labeled compound can be obtained.

Effect of the Invention

As mentioned above, according to the method of rapid methylation of an aromatic compound or an alkenyl compound of the present invention, it is possible to obtain an aromatic compound or an alkenyl compound labeled with a $^{11}$C-labeled methyl group or a $^{18}$F-labeled fluoromethyl group rapidly and in a high yield under mild conditions by using a not so highly toxic organic boron compound as a substrate.

BEST MODE OF CARRYING OUT THE INVENTION

Hereinafter, Examples of the exemplary embodiment of the present invention are described in detail in comparison with Comparative Examples. Note here that in the description below, Pd$_2$(dba)$_3$ represents tris(dibenzylideneacetone)dipalladium. Furthermore, P(o-tolyl)$_3$ represents tri-o-tolylphosphine, and P(t-Bu)$_2$Me represents (di-t-butyl)methylphosphine, and DMF represents N,N-dimethylformamide, respectively.

Furthermore, in the present specification, a phosphine ligand is not particularly limited as long as it is a compound for catalyzing the reaction of the present invention. For example, in addition to tri-o-tolylphosphine and (di-t-butyl)methylphosphine, it includes any compounds in which electronic and three-dimensional effects are sequentially changed depending upon the kinds of substituents bonded to P-atom and encompasses a two-conformational ligand, a multi-conformational ligand and an asymmetrical type chelate ligand.

In Comparative Examples 1 to 3 and Examples 1 to 6, methylations of methyl iodide of phenyl boronic acid pinacol ester 1 shown in Table 1 were carried out under various conditions. The charge amount was made to be as follows: phenyl boronic acid pinacol ester 1: 400 μmol, palladium complex: 10 μmol, and methyl iodide: 10 μmol. The details are shown below.

Comparative Examples 1-3

In Comparative Examples 1-3, under well-known conditions, methylation of methyl iodide of phenyl boronic acid pinacol ester 1 was carried out. That is to say, in Comparative Example 1, Pd(PPh$_3$)$_4$ was used as a palladium (0) complex, potassium carbonate was used as a base, and 1,4-dioxane was used as a solvent. Furthermore, in Comparative Example 2, PdCl$_2$(PPh$_3$)$_2$ was used as a palladium (0) complex, potassium phosphate was used as a base, and a solvent of ethylene glycol dimethyl ether/water=9/1 was used as a solvent. Furthermore, in Comparative Example 3, PdCl$_2$ (dppf)$_2$ was used as a palladium (0) complex, potassium phosphate was used as a base, and a solvent of ethylene glycol dimethyl ether/water=9/1 was used as a solvent. Furthermore, the reaction temperature was made to be 60° C. and the reaction time was made to be 5 minutes. As a result, in any reaction conditions, the yield was low (24 to 39%) (Table 1, Comparative Examples 1-3).

Examples 1-6

On the other hand, in Examples 1-6 of Table 1 in which a bulky phosphine ligand was added in addition to a palladium (0) complex and a base and DMF was used as an aprotic polar solvent, the reaction was dramatically promoted and the intended toluene was obtained in such a high yield as 87-94% (Table 1, Examples 1-6).

TABLE 1

Rapid capture reaction of methyl iodide by using phenyl boronic acid pinacol ester CH$_3$I + [phenyl boronic acid pinacol ester structure] $\xrightarrow[\text{5 minutes, 60° C.}]{\text{Pd, additive}}$ 1
40 equivalents

[toluene product structure with CH$_3$]

| | Pd(0) complex | ligand | Pd:L [mole ratio] | base$^b$ | solvent (1.0 ml) | yield (%)$^c$ |
|---|---|---|---|---|---|---|
| Comparative Example 1 | Pd(PPh$_3$)$_4$ | — | — | K$_2$CO$_3$ | 1,4-dioxane | 39 |
| Comparative Example 2 | PdCl$_2$(PPh$_3$)$_2$ | — | — | K$_3$PO$_4$ | DME/H$_2$O = 9/1 | 24 |
| Comparative Example 3 | PdCl$_2$(dppf)$_2$ | — | — | K$_3$PO$_4$ | DME/H$_2$O = 9/1 | 28 |
| Example 1 | Pd$_2$(dba)$_3$ | P(o-CH$_3$C$_6$H$_4$)$_3$ | 1:2 | K$_2$CO$_3$ | DMF | 91 |
| Example 2 | Pd$_2$(dba)$_3$ | P(o-CH$_3$C$_6$H$_4$)$_3$ | 1:2 | K$_2$CO$_3$ | DMF/H$_2$O = 9/1 | 94 |
| Example 3 | Pd$_2$(dba)$_3$ | P(o-CH$_3$C$_6$H$_4$)$_3$ | 1:2 | Cs$_2$CO$_3$ | DMF | 92 |
| Example 4 | Pd$_2$(dba)$_3$ | P(o-CH$_3$C$_6$H$_4$)$_3$ | 1:2 | K$_3$PO$_4$ | DMF | 87 |
| Example 5 | Pd$_2$(dba)$_3$ | P(o-CH$_3$C$_6$H$_4$)$_3$ | 1:2 | CuCl/K$_2$CO$_3$ | DMF | 81 |
| Example 6 | Pd$_2$(dba)$_3$ | P(o-CH$_3$C$_6$H$_4$)$_3$ | 1:2 | KF | DMF | 81 |

(Description of Table 1)
$^b$20 μmol of base was used
$^c$yield was calculated based on methyl iodide as a reference by using GC analysis DME: diethylene glycol dimethyl ether, DMF: N,N-dimethylformamide, dba: dibenzylideneacetone, dppf: 1,1'-bis(diphenylphosphino)ferrocene A coupling reaction between methyl iodide and phenyl boronic acid pinacol ester 1 is estimated to proceed via the following four elementary reactions as shown in the following reaction formulae in the presence of potassium carbonate or potassium carbonate/water.

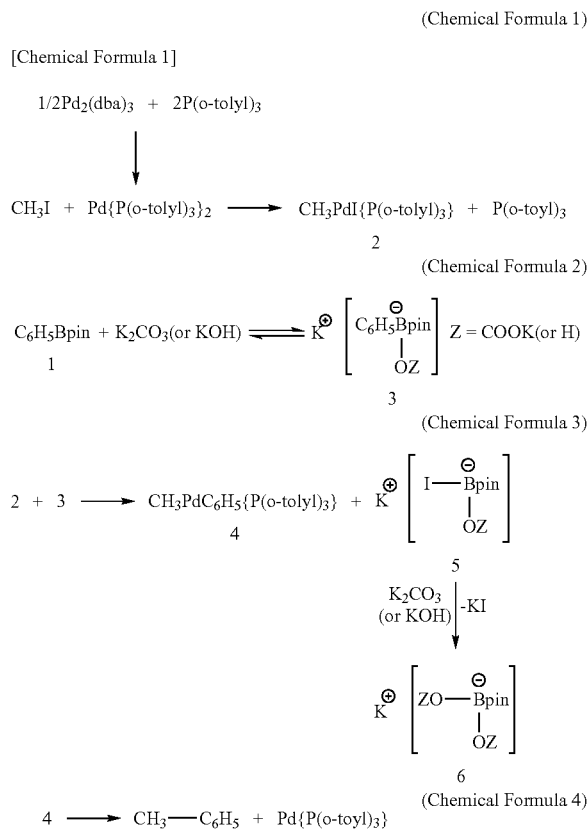

That is to say,
(1) Methyl iodide is oxidatively added to a palladium (0) complex and methyl palladium (II) complex 2 is formed (Formula 1).
(2) Furthermore, boron ate complex 3 is formed in which carbonate ion or hydroxide ion generated from a mixture system of potassium carbonate/water or COOK$^-$ is coordinated to a boron atom of phenyl boronic acid pinacol ester 1 and the polarity between B and C is heightened (Formula 2).
(3) Then, the methyl palladium (II) complex 2 and the boron ate complex 3 cause transmetalation, so that methyl phenyl palladium (II) complex 4 is formed. Furthermore, unstable B$^-$(pin)(OZ)(I) 5 (Z=COOK or H) generated at this time is converted into B$^-$(pin)(OZ)$_2$ 6 that is a more stable boron ate complex and KI (Formula 3).
(4) Finally, the methyl phenyl palladium (II) complex 4 causes a reductive release reaction and generates an intended toluene (Formula 4).

In order to promote the coupling reaction between carbon of the benzene ring and SP$^3$ carbon, it is important to form a coordinatively-unsaturated palladium (0) complex whose ligand is a bulky tri-o-phosphine (cone angle: 194°) and a palladium (II) complex in a reaction precess. Furthermore, potassium carbonate or cesium carbonate or potassium phosphate as a base is estimated to play a role as a synergistic material for activating boron and neutralizing the reaction system after transmetalation. Furthermore, DMF is estimated to contribute to stabilization of a palladium intermediate product formed in the reaction system.

Examples 7-19

In Examples 7-19, as the aromatic boronic acid ester, boronic pinacol esters (400 µmol) to which various aromatic rings shown in Table 2 are bonded were used as a substrate. The other conditions were made to be the same as in the above-mentioned Example 1, that is to say, methyl iodide (10 µmol), tris(dibenzylideneacetone) dipalladium complex (0) (5 µmol), tri-o-tolylphosphine (20 µmol) and potassium carbonate (20 µmol) were used, and DMF was used as a solvent (in Example 12, DMF/water=9/1 was also used).

As a result, a methyl group was able to be bonded to various aromatic rings as shown in Table 2 in an extremely high yield. With respect to these aromatic rings, it was possible to carry out methylation in a high yield to a heterocycle such as a thiophenyl group shown in Example 14 or a furanyl group shown in Example 15 besides the benzene rings to which substituents shown in Examples 7-13 are bonded. Furthermore, it is remarkable that it is possible to carry out methylation in a high yield with respect to a heterocycle having strong basicity like a pyridinyl group of Example 16 or an isoquinolinyl group of Example 17. It is shown that the rapid methylation of the aromatic compound of the present invention is excellent in versatility.

Furthermore, the reaction under the condition in which 5-10 equivalents of the palladium (0) complex and the potassium carbonate had been added to the methyl iodide was investigated. The ratio of CH$_3$I/phenyl boronic acid pinacol ester/Pd$_2$(dba)$_3$/P(o-tolyl)$_3$/K$_2$CO$_3$ was made to be 1:40:2.5:10:10 or 1:40:5:20:20, and the reaction was carried out at 60° C. for 5 minutes. As a result, toluene was obtained in the yield of 92% and 94%. Thus, even when an excessive amount of palladium (0) complex was used, the methylation was not prevented and it was rather promoted. This is preferable because in actual PET methods, an excessive amount of palladium (0) complex must be used since only an extremely small amount of labeled methyl iodide can be obtained.

TABLE 2

Rapid methylation reaction of aryl boronic acid pinacol ester

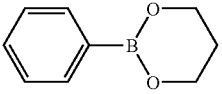

| | R | yield of methylated product (%)[b] R—CH$_3$ |
|---|---|---|
| Example 7 | 4-CH$_3$OC$_6$H$_4$— | 98 |
| Example 8 | 3-benzyloxyC$_6$H$_4$— | 95 |
| Example 9 | 4-CH$_3$C$_6$H$_4$— | 99 |
| Example 10 | 4-PhC$_6$H$_4$— | 91 |
| Example 11 | 4FC$_6$H$_4$— | 93 |
| Example 12 | 4-CH$_3$OCOC$_6$H$_4$— | 82, 96[c] |
| Example 13 | 4-NO$_2$C$_6$H$_4$— | 99 |
| Example 14 | thiophen-2-yl- | 92 |
| Example 15 | furan-2-yl- | 85 |
| Example 16 | pyridin-4-yl- | 80 |
| Example 17 | isoquinolin-4-yl | 85 |
| Example 18 | | toluene: 92% |

TABLE 2-continued

Rapid methylation reaction of aryl boronic acid pinacol ester

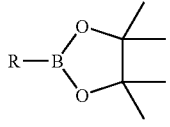

| R | yield of methylated product (%)[b] R—CH$_3$ |
|---|---|
| Example 19 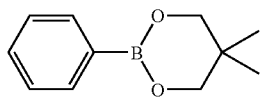 | toluene: 95% |

(Description of Table 2)
[b]yield was calculated by GC analysis based on methyl iodide as a reference.
[c]mixed solvent (DMF : H$_2$O = 9:1) was used.

Examples 20-25

In Examples 20-25, as the alkenyl boronic acid pinacol ester, boronic acid pinacol esters (400 μmol) in which various alkenyl groups are bonded shown in Table 3 were used as a substrate and other conditions were made to be the same as those in the above-mentioned Example 1. That is to say, methyl iodide (10 μmol), tris(dibenzylideneacetone) dipalladium complex (0) (5 μmol), tri-o-tolylphosphine (20 μmol) and potassium carbonate (20 μmol) were used and DMF was used (however, in Example 12, DMF/water=9/1 was also used)).

As a result, a methyl group was able to be bonded to various alkenyl groups shown in Table 3 in an extremely high yield. Furthermore, as is apparent from the results of Examples 20 and 21 in which cis- and trans-alkenyl compounds were used, it was confirmed that with respect to the cis- and trans-stereoisomers, an intended methylated product was obtained while maintaining the stereochemical structure, and that the reaction proceeded under the complete stereocontrol, according to the rapid methylation method of an alkenyl compound of the present invention.

TABLE 3

Capture reaction of methyl iodide by alkenyl boronic acid pinacol ester

| | alkenyl boronic acid pinacol ester | yield of methylated product (%)[b] |
|---|---|---|
| Example 20 | 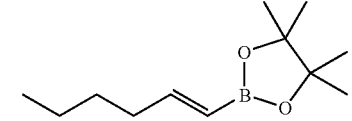 | 95 |
| Example 21 |  | 92 |
| Example 22 | 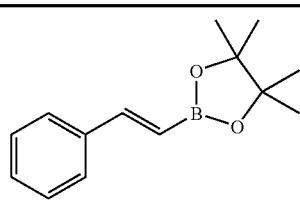 | 96 |
| Example 23 | 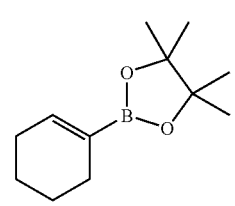 | 86 |
| Example 24 | 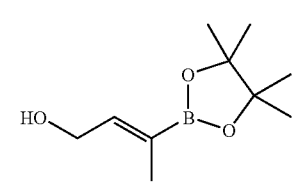 | 99 |
| Example 25 | 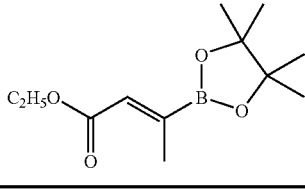 | 99 |

(Description of Table 3)
The reaction was carried out by using methyl iodide (10 μmol), an alkenyl boronic acid pinacol ester (400 μmol), tris(dibenzylideneacetone) dipalladium complex (0) (5 μmol, tri-o-tolylphosphine (20 μmol, and potassium carbonate (20 μmol).
[b]yield was calculated by GC analysis based on methyl iodide as a reference.

<Retention Time of Organic Boron Compound by HPLC>

When rapid methylation was carried out by using labeled methyl iodide and then the intended methylated compound was isolated by HPLC, it is preferable that the retention time of an organic boron compound as a substrate and the retention time of the intended methylated compound are as different as possible. Furthermore, since the organic boron compound as a substrate is used in an excessive amount, it is preferable that the retention time of the intended compound is shorter than the retention time of the organic boron compound as a substrate. This is because when the retention time of the intended compound is longer than the retention time of the organic boron compound as a substrate, a peak of the intended compound is overlapped in the tailing of the excessive amount of the organic boron compound, thus making it difficult to isolate the intended compound.

The retention time was measured in HPLC using a reverse-phase silica gel by using the following compound ((a): phenyl boronic acid, (b)-(d): a phenyl boronic acid ester of various pinacol) as an organic boron compound in which a phenyl group is bonded to boron.

[Chemical Formula 2]

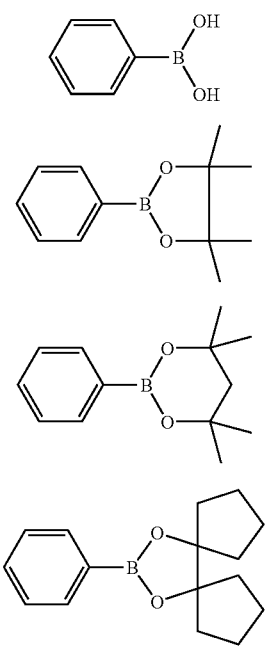

As a result, each retention time was (a) 2.1 minutes, (b) 10.0 minutes, (c) 21.5 minutes, and (d) 43.1 minutes, respectively. In this way, the retention times of boron acid derivatives in HPLC are longer as the liposolubility of the boron compound is increased. By selecting a boronic acid ester having high liposolubility, purification of a tracer can be carried out more easily. In this experiment, the retention time of toluene that is a methylated product (5.9 minutes) appears between the retention time of the boron acid (a) and the boronic acid esters (b)-(d). This means that a boronic acid ester is more desirable than a boronic acid in synthesis of a PET tracer. Note here that the methylation reaction of compounds (a), (c) and (d) proceed smoothly, and the methylated products could be obtained in such high yields of 89, 79 and 87%, respectively.

<Rapid Methylation of Aromatic Compound by $FCH_2I$ (Fluoroiodomethane)>

[Chemical Formula 3]

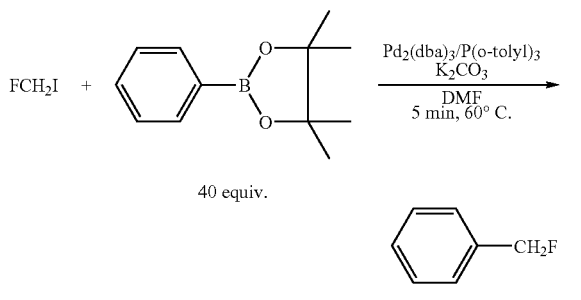

to 57% (average yield: 47%)
Capture reaction of fluoromethyl iodide by penyl boronic acid pinacol ester As shown in the above-mentioned reaction formula, the rapid fluoromethylation of a phenyl boronic acid pinacol ester by $FCH_2I$ (fluoroiodomethane) was tried. As a result, it was shown that the reaction proceeded for five minutes in a high yield. Furthermore, in order to promote the fluoromethylation reaction, it was determined that the reaction in the ratio of Pd:P(o-tolyl)$_3$=1:3 was effective. In this reaction, benzyl fluoride as the intended substance was obtained in a yield of 57% at maximum (average yield: 47%). Note here that although the same reaction was carried out by using a tin compound, the intended product was obtained only in a low yield (20-30%). The above-mentioned results showed that $^{18}$F-labeled fluoroiodomethane ($^{18}FCH_2I$) as a labeling precursor was able to be applied for the study of the $^{18}$F-labeled PET tracer without losing a high initial specific radioactivity of $^{18}$F.

<Synthesis of $^{11}$C-Labeled Xylene>

By considering the application to a PET method, when the rapid methylation of p-tolyl phenyl boronic acid pinacol ester by using methyl iodide that had been actually labeled with $^{11}$C as a methylation substance (the reaction conditions were made to be the same as in Example 1 (see, Table 1)), $^{11}$C-labeled xylene was obtained in such a high yield of 96% (value by HPLC analysis) (see the following reaction formula). FIG. 1 shows the analysis results by a high speed liquid chromatography of $^{11}$C methyl-labeled xylene. Furthermore, in this reaction, it was shown that the yield became higher when potassium carbonate was used as a base as compared with the case where KF or CsF was used. From the above-mentioned results, it was shown that the method of rapid methylation of the present invention was extremely useful for producing a $^{11}$C-labeled PET tracer.

[Chemical Formula 4]

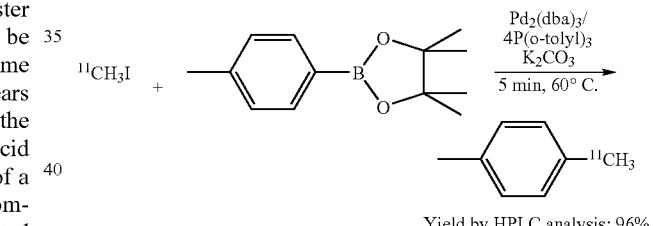

Yield by HPLC analysis: 96%
Synthesis of [$^{11}$C]-containing compound by rapid methylation reaction As the labeled methyl iodide in the present invention, compounds labeled with not only $^{11}$C but also $^{13}$C, $^{14}$C, $CD_3$ and the like can be used. By using methyl iodide labeled with any one of $^{11}$C, $^{13}$C, $^{11}$C and $CD_3$, labeled molecular probes can be prepared. This labeled molecular probe can be effectively used for study of metabolism of drugs, research and development of new drugs.

Hereinafter, when the method of rapid methylation for preparing a compound containing a methyl group of the present invention is used, it is assumed that a kit and a clinical administration solution can be provided with high feasibility. It is determined that the exemplary embodiments shown below can be naturally realized based on the highly specific knowledge of the present inventors.

Kit for Preparing PET Tracer

First Exemplary Embodiment

The method of rapid methylation of an aromatic compound or an alkenyl compound in accordance with the present invention can provide a kit for preparing a PET tracer. For example, the following kit for preparing a PET tracer can be included. That is to say, a kit for preparing a PET tracer of the first exemplary embodiment is obtained by measuring 1.8 mg (1.97 µmol) of tris(dibenzylideneacetone) dipalladium (0), 2.4 mg (7.88 µmol) of tri-o-tolylphosphine, 2.8 mg (20 µmol) of potassium carbonate, and 4.5 µmol of an alkenyl boronic acid pinacol ester (or aromatic boronic acid pinacol ester) and charging them in an ampule tube.

This kit is used as follows. That is to say, an ampule tube is cut by a glass cutter and a predetermined amount of an aprotic polar solvent such as DMF is added so as to dissolve the reagents in the ampule tube. Furthermore, $^{11}$C-labeled methyl iodide that has been separately prepared is introduced in the solution and mixed, and then the mixture is placed in a warm bath at 60° C. for five minutes so as to be reacted. Then, the ampule tube taken out from the warm bath is cooled and then the reaction solution is filtrated through an appropriate solid phase extraction column. The filtrate is subjected to HPLC. Thus, it is possible to obtain an intended $^{11}$C methyl-labeled compound that has been separated and purified.

Second Exemplary Embodiment

In a kit for preparing a PET tracer of a second exemplary embodiment, a solid phase extraction column is provided to the kit for preparing a PET tracer of the first exemplary embodiment. Thus, it is not necessary to additionally prepare a solid phase extraction column for pre-treatment.

Third Exemplary Embodiment

A kit for preparing a PET tracer of a third exemplary embodiment includes two kinds of ampule tubes, that is, an ampule tube A and an ampule tube B. The ampule tube A has a capacity of 0.5 ml and filled with tris(dibenzylideneacetone) dipalladium (0) (1.97 µmol) and tri-o-tolylphosphine (7.9 µmol). On the other hand, the ampule tube B has a capacity of 1.0 ml and filled with an organic boron compound (4.5 µmol) and potassium carbonate (20 µmol).

This kit is used as follows. That is to say, an ampule tube A is cut by a glass cutter and a predetermined amount of an aprotic polar solvent such as DMF is added so as to dissolve the reagents in the ampule tube A. Similarly, an ampule tube B is cut by a glass cutter and a predetermined amount of an aprotic polar solvent such as DMF is added so as to dissolve the reagents in the ampule tube B. Then, separately prepared $^{11}$C-labeled methyl iodide is introduced in the solution in the ampule tube A in which the reagents have been dissolved and are mixed. Then, the mixture is reacted in a warm bath at 60° C. for five minutes. Then, the ampule tube A taken out from the warm bath is cooled, the reaction solution is introduced into the ampule tube B, the inside of the ampule tube A is washed with 40 µl of DMF, and this washing solution was placed in the ampule tube B. Then, the mixture in the ampule tube B is heated at 65° C. for five minutes, then a DMF:H$_2$O (1:5) solution (300 µl) is used and the reaction solution is filtrated by subjecting the reaction solution to cotton plug filtration or a SPE solid phase extraction column. Furthermore, an intended compound in the filtrate is separated and purified by HPLC. The aliquot of a $^{11}$C-labeled compound is concentrated by an evaporator and then a predetermined clinical administration solution can be made.

In the method of rapid methylation of the present invention, not only a one-pot synthesis but also a two-pot synthesis can be used.

Herein, the one-pot synthesis means a method of reacting methyl iodide or X—CH$_2$F (wherein X represents a functional group that can be easily released as an anion), an organic boron compound in which an aromatic ring or an alkenyl group are bonded to boron, a palladium (0) complex, a phosphine ligand, and a base with each other in a single vessel at one time.

On the other hand, the two-pot synthesis means a method of rapid methylation of an aromatic compound or an alkenyl compound, which includes a palladium complex preparation step of obtaining a Pd complex solution by reacting methyl iodide or X—CH$_2$F (wherein X represents a functional group that can be easily released as an anion), a palladium (0) complex, and a phosphine ligand with each other in an aprotic polar solvent;

a boron ate complex preparation step of obtaining a boron ate complex solution by reacting an organic boron compound in which an aromatic ring or an alkenyl group is bonded to boron and a base with each other in an aprotic polar solvent; and a coupling step of mixing and cross-coupling the Pd complex solution and the boron ate complex solution.

That is to say, in the two-pot synthesis, a vessel in which the palladium complex preparation step is carried out and a vessel in which the boron ate complex preparation step is carried out are distinguished from each other, and the reaction solutions of the respective vessels (that is to say, a Pd complex solution and a boron ate complex solution) are mixed with each other and cross coupling is carried out.

Hereinafter, the method of rapid methylation of an aromatic compound or an alkenyl compound of the present invention is described with reference to Examples describing further details of the reacting conditions. The present invention is not limited to the description of the following Examples. A variety of modifications can be made as long as they are within the scope of the contents of the present invention. Such modifications are also encompassed in the present invention.

Example 26

Tris(dibenzylideneacetone) dipalladium (0) (5 µmol), tri-o-tolylphosphine (20 µmol), and potassium carbonate (20 µmol) were placed in a 10-ml volume dry Schlenk tube as a reactor vessel under argon atmosphere, and a DMF (N, N-dimethylformamide) solvent (0.5 ml) was added thereto. The mixture was stirred at room temperature for 5 minutes. Then, a DMF solution (0.5 mL) of phenyl boronic acid pinacol ester (400 µmol) and a DMF solution of methyl iodide (10 µmol) were subsequently added so as to cause reaction at 60° C. for five minutes. The reactor vessel was cooled quickly by using ice bath so as to stop the reaction, then, diethyl ether (1 mL) was added to the reaction solution. Then the mixture was loaded on a short column of silica gel (0.5 g) and eluted with diethyl ether (1 mL). Next, n-nonane (50 µl, 0.01M DMF solution, 5.0 µmol) as an internal standard substance was added to the eluted solution, which was subjected to a gas chromatography. As a result, the intended $^{11}$C-labeled toluene was obtained in a yield of 91% with reference to methyl iodide.

Conditions of Gas Chromatography Analysis

Gas chromatograph equipped with hydrogen flame ionization detector (FID detector)

GC-2010 produced by Shimazu; Capillary column: TC-1701 produced by GLScience (length: 60 m, inner diameter: 0.25 mm)

Carrier gas: helium; Flow rate: 0.55 mL/min; Linear velocity: 14.2 cm/min

Temperature of sample introducing part and detector: 280° C.

Temperature of column: initial temperature: 80° C., final temperature: 200° C. The temperature is increased at 5° C./min from 10th to 14th minutes, and increased at 20° C./min from 20th to 25th minutes Retention time: toluene (13.0 min)

Example 27

Tris(dibenzylideneacetone) dipalladium (0) (5 μmol), tri-o-tolylphosphine (30 μmol), and potassium carbonate (20 μmol) were placed in a 10-ml volume dry Schlenk tube as a reactor vessel under argon atmosphere, and a DMF (N, N-dimethylformamide) solvent (0.5 ml) was added thereto, a DMF solution of phenyl boronic acid pinacol ester (400 μmol), and a DMF solution of $^{18}$F-labeled fluoroiodomethane (10 μmol) were sequentially added and mixed so as to react at 60° C. for five minutes.

The reactor vessel was cooled quickly by using ice bath so as to stop the reaction, then, diethyl ether (1 mL) was added to the reaction solution, loaded on a short column of silica gel (0.5 g) and eluted with diethyl ether (1 mL) as an eluted solution. As an internal standard substance, n-nonane (50 μl, 0.10M DMF solution, 5.0 μmol) was added to the eluted solution, which was subjected to a GLC analysis. As a result, the intended benzyl fluoride was obtained in a yield of 57% (average yield of 47%) with reference to fluoroiodomethane.

Conditions of Gas Chromatography Analysis

Gas chromatograph equipped with hydrogen flame ionization detector (FID detector)

GC-2010 produced by Shimazu; Capillary column: TC-1701 produced by GLScience (length: 60 m, inner diameter: 0.25 mm)

Carrier gas: helium; Flow rate: 0.55 mL/min; Linear velocity: 14.2 cm/min

Temperature of sample introducing part and detector: 280° C.

Temperature of column: initial temperature: 70° C., final temperature: 200° C. The temperature is increased at 10° C./min from 5th to 9th minutes, and increased at 20° C./min from 17th to 22th minutes Retention time: benzyl fluoride (13.9 min)

Example 28

Tris(dibenzylideneacetone) dipalladium (0) (25 μmol), tri-o-tolylphosphine (100 μmol), and potassium carbonate (100 μmol) were placed in a 10-ml volume of dry Schlenk tube as a reactor vessel under argon atmosphere, and a DMF (N,N-dimethylformamide) solvent (0.5 ml) was added thereto, a DMF solution of phenyl boronic acid pinacol ester 1 (400 μmol), and a DMF solution (0.5 mL) of methyl iodide (10 μmol) were added sequentially and they were mixed and reacted at 60° C. for five minutes.

The reactor vessel was cooled quickly by using ice bath so as to stop the reaction, diethyl ether (1 mL) was then added to the reaction solution, loaded on a short column of silica gel (0.5 g) and eluted with diethyl ether (1 mL). As an internal standard substance, n-nonane (50 μl, 0.01M DMF solution, 5.0 μmol) was added to the eluted solution, which was subjected to a gas chromatography analysis. As a result, the intended toluene was obtained in a yield of 92% with reference to methyl iodide.

Conditions of Gas Chromatography Analysis

Gas chromatograph equipped with hydrogen flame ionization detector (FID detector)

GC-2010 produced by Shimazu; Capillary column: TC-1701 produced by GLScience (length: 60 m, inner diameter: 0.25 mm)

Carrier gas: helium; Flow rate: 0.55 mL/min; Linear velocity: 14.2 cm/min

Temperature of sample introducing part and detector: 280° C.

Temperature of column: initial temperature: 80° C., final temperature: 200° C. The temperature is increased at 5° C./min from 10th to 14th minutes, and increased at 20° C./min from 20th to 25th minutes Retention time: toluene (13.0 min)

Example 29

Tris(dibenzylideneacetone) dipalladium (0) (50 μmol), tri-o-tolylphosphine (200 μmol), and potassium carbonate (200 μmol) were placed in a 10-mL volume dry Schlenk tube as a reactor vessel under argon atmosphere, a DMF (N, N-dimethylformamide) solvent (0.5 mL) was added thereto, a DMF solution (0.5 mL) of phenyl boronic acid pinacol ester (400 μmol), and a DMF solution of methyl iodide (10 μmol) were added sequentially. They were mixed and reacted with each other at 60° C. for five minutes. The reactor vessel was cooled quickly by using ice bath so as to stop the reaction, diethyl ether (1 mL) was then added to the reaction solution, the solution was loaded on a short column of silica gel (0.5 g) and eluted with diethyl ether (1 mL).

As an internal standard substance, n-nonane (50 μl, 0.01M DMF solution, 5.0 μmol) was added to the eluted solution, which was subjected to a gas chromatography analysis. As a result, the intended toluene was obtained in a yield of 94% with reference to methyl iodide.

Conditions of Gas Chromatography Analysis

Gas chromatograph equipped with hydrogen flame ionization detector (FID detector)

GC-2010 produced by Shimazu; Capillary column: TC-1701 produced by GLScience (length: 60 m, inner diameter: 0.25 mm)

Carrier gas: helium; Flow rate: 0.55 mL/min; Linear velocity: 14.2 cm/min

Temperature of sample introducing part and detector: 280° C.

Temperature of column: initial temperature: 80° C., final temperature: 200° C. The temperature is increased at 5° C./min from 10th to 14th minutes, and increased at 20° C./min from 20th to 25th minutes Retention time: toluene (13.0 min)

Example 30

In a 0.5 mL-volume reactor vessel, p-tolyl boronic acid pinacol ester (1.7-1.8 mg, 8.0 μmol) used in Example 9 of Table 2, tris(dibenzylideneacetone) dipalladium (2.9 mg, 3.17 μmol), tri-o-tolylphosphine (3.8 mg, 12.7 μmol) and a DMF solution (0.45 mL) of potassium carbonate (1.0 mg, 7.2 μmol) were placed and set at room temperature.

In this reactor vessel, $^{11}$C methyl iodide was captured at room temperature and stood still for one minute. The resultant mixture solution was heated at 65° C. for five minutes and then a DMF:H$_2$O (1:5) solution (300 μl) was used so as to filter the reaction solution through a cotton plug (or by a SPE solid phase extraction column). The filtrate was subjected to HPLC and the intended $^{11}$C methylated product was separated and purified. The yield of the HPLC analysis of the intended $^{11}$C xylene was 96%.

Example 31

The synthesis reaction can be carried out by either one of the above-mentioned one-pot operation and the two-pot operation.

The synthesis of the above-mentioned $^{11}$C methylated product can be carried out by using a general PET tracer synthesizing apparatus such as a solution transferring type synthesizing apparatus or a robot arm type synthesizing apparatus. Furthermore, a PET tracer synthesis kit for the purpose of synthesizing the above-mentioned $^{11}$C methylated product can be produced. The synthesis kit includes necessary amounts of reaction agents, an organic boron compound and a DMF solvent which are placed in each reactor vessel, and in the kit, synthesis of the intended $^{11}$C methylated product is carried out by transferring a solution through a septum-cannulation method by remote control.

INDUSTRIAL APPLICABILITY

The invention of the present application can be used in the medical industries, and the like, as a method of producing a PET tracer.

BRIEF DESCRIPTION OF THE DRAWINGS

FIG. 1 shows the results analyzed by a high-performance liquid chromatography of $^{11}$C-labeled xylene.

The invention claimed is:

1. A method of rapid methylation of an aromatic compound or an alkenyl compound, the method comprising;
   cross-coupling methyl iodide or X—$CH_2F$, wherein X is a functional group that can be released as an anion, and an organic boron compound in which an aromatic ring or an alkenyl group is bonded to boron in an aprotic polar solvent in the presence of a palladium (0) complex, a phosphine ligand, wherein the phosphine ligand is tri-o-tolylphosphine or (di-t-butyl)methylphosphine, and a base.

2. The method of rapid methylation of an aromatic compound or an alkenyl compound according to claim 1, wherein the phosphine ligand makes the palladium (0) complex be a coordinatively-unsaturated complex.

3. The method of rapid methylation of an aromatic compound or an alkenyl compound according to claim 1, wherein the cross-coupling is carried out by the following procedure:
   a palladium complex activation step of carrying out ligand exchange between the palladium (0) complex and the phosphine ligand to form an active palladium (0) complex;
   an oxidative addition step of forming a methyl palladium (II) complex or a $CH_2F$ palladium (II) complex by oxidatively adding the methyl iodide or the X—$CH_2F$, wherein X is a functional group that can be released as an anion, to said active palladium (0) complex;
   an ate complex formation step of forming a boron ate complex by allowing the base to be coordinated to a boron atom of said organic boron compound in which the aromatic ring or the alkenyl group is bonded to the boron;
   a transmetalation step of carrying out a transmetalation reaction of the methyl palladium (II) complex or the $CH_2F$ palladium (II) complex and the boron ate complex so as to form a palladium (II) complex in which a methyl group or a $CH_2F$ group and the aromatic ring or the alkenyl group are bonded to palladium; and
   a step of causing a reductive release reaction of the palladium (II) complex in which the methyl group or the $CH_2F$ group and the aromatic ring or the alkenyl group are bonded to palladium so as to be cross-coupled.

4. The method of rapid methylation of an aromatic compound or an alkenyl compound according to claim 1, wherein the methyl iodide and the organic boron compound are reacted with each other.

5. The method of rapid methylation of an aromatic compound or an alkenyl compound according to claim 4, wherein the palladium (0) complex is tris(dibenzylideneacetone) dipalladium (0).

6. The method of rapid methylation of an aromatic compound or an alkenyl compound according to claim 4, wherein said organic boron compound in which the aromatic ring or the alkenyl group is bonded to the boron, the palladium (0) complex, and the phosphine ligand and the base are used in not less than an equivalent amount with respect to the methyl iodide.

7. The method of rapid methylation of an aromatic compound or an alkenyl compound according to claim 4, wherein the phosphine ligand is not less than four times the palladium (0) complex in a mole ratio.

8. The method of rapid methylation of an aromatic compound or an alkenyl compound according to claim 1, wherein the phosphine ligand is tri-o-tolylphosphine, the palladium (0) complex is tris(dibenzylideneacetone) dipalladium (0), and the methyl iodide and the organic boron compound are reacted with each other.

9. The method of rapid methylation of an aromatic compound or an alkenyl compound according to claim 8, wherein the base is potassium carbonate.

10. The method of rapid methylation of an aromatic compound or an alkenyl compound according to claim 1, wherein the X—$CH_2F$ and the organic boron compound are reacted with each other.

11. The method of rapid methylation of an aromatic compound or an alkenyl compound according to claim 10, wherein the palladium (0) complex is tris(dibenzylideneacetone) dipalladium (0).

12. The method of rapid methylation of an aromatic compound or an alkenyl compound according to claim 10, wherein the organic boron compound in which the aromatic ring or the alkenyl group is bonded to the boron, the palladium (0) complex, the phosphine ligand and the base are used in not less than an equivalent amount with respect to X—$CH_2F$.

13. The method of rapid methylation of an aromatic compound or an alkenyl compound according to claim 10, wherein the phosphine ligand is not less than three times the palladium (0) complex in a mole ratio.

14. The method of rapid methylation of an aromatic compound or an alkenyl compound according to claim 1, wherein the phosphine ligand is tri-o-tolylphosphine, the palladium (0) complex is tris(dibenzylideneacetone) dipalladium (0), X—$CH_2F$ is $CH_2FI$, and the $CH_2FI$ and said organic boron compound are reacted with each other.

15. The method of rapid methylation of an aromatic compound or an alkenyl compound according to claim 14, wherein the base is potassium carbonate.

16. The method of rapid methylation of an aromatic compound or an alkenyl compound according to claim 1, wherein said organic boron compound in which the aromatic ring or the alkenyl group is bonded to the boron is an aromatic boronic acid ester or an alkenyl boronic acid ester.

17. The method of rapid methylation of an aromatic compound or an alkenyl compound according to claim 1, wherein the base is a carbonate or a phosphate.

18. The method of rapid methylation of an aromatic compound or an alkenyl compound according to claim 1, wherein the aromatic ring includes a heterocycle.

19. A method of producing a PET tracer, the method comprising;
cross-coupling methyl iodide or X—$CH_2F$, wherein X is a functional group that can be released as an anion, which is labeled with a carbon isotope other than $^{12}C$ or a hydrogen isotope other than $^{1}H$, and an organic boron compound in which an aromatic ring or an alkenyl group is bonded to boron in an aprotic polar solvent in the presence of a palladium (0) complex, a phosphine ligand, wherein the phosphine ligand is tri-o-tolylphosphine or (di-t-butyl)methylphosphine, and a base.

20. The method of producing a PET tracer according to claim 19, wherein the phosphine ligand makes the palladium complex (0) be a coordinatively-unsaturated complex.

21. The method of producing a PET tracer according to claim 19, wherein the cross-coupling is carried out by the following procedure:
a palladium complex activation step of carrying out ligand exchange between the palladium (0) complex and the phosphine ligand to form an active palladium (0) complex;
an oxidative addition step of forming a methyl palladium (II) complex or a $CH_2F$ palladium (II) complex by oxidatively adding the methyl iodide or the X—$CH_2F$, wherein X is a functional group that can be released as an anion, to said active palladium (0) complex;
an ate complex formation step of forming a boron ate complex by allowing the base to be coordinated to a boron atom of said organic boron compound in which the aromatic ring or the alkenyl group is bonded to the boron;
a transmetalation step of carrying out a transmetalation reaction of the methyl palladium (II) complex or the $CH_2F$ palladium (II) complex and the boron ate complex so as to form a palladium (II) complex in which a methyl group or a $CH_2F$ group and the aromatic ring or the alkenyl group are bonded to palladium; and
a step of causing a reductive release reaction of the palladium (II) complex in which the methyl group or the $CH_2F$ group and the aromatic ring or the alkenyl group are bonded to palladium so as to be cross-coupled.

22. The method of producing a PET tracer according to claim 19, wherein the methyl iodide and the organic boron compound are reacted with each other.

23. The method of producing a PET tracer according to claim 22, wherein the palladium (0) complex is tris(dibenzylideneacetone) dipalladium (0).

24. The method of producing a PET tracer according to claim 22, wherein said organic boron compound in which the aromatic ring or the alkenyl group is bonded to the boron, the palladium (0) complex, the phosphine ligand and the base are used in not less than an equivalent amount with respect to the methyl iodide.

25. The method of producing a PET tracer according to claim 22, wherein the phosphine ligand is not less than four times the palladium (0) complex in a mole ratio.

26. The method of producing a PET tracer according to claim 19, wherein the phosphine ligand is tri-o-tolylphosphine, the palladium (0) complex is tris(dibenzylideneacetone) dipalladium (0), and the methyl iodide and the organic boron compound are reacted with each other.

27. The method of producing a PET tracer according to claim 26, wherein the base is potassium carbonate.

28. The method of producing a PET tracer according to claim 19, wherein the X—$CH_2F$ and the organic boron compound are reacted with each other.

29. The method of producing a PET tracer according to claim 28, wherein the palladium (0) complex is tris(dibenzylideneacetone) dipalladium (0).

30. The method of producing a PET tracer according to claim 28, wherein said organic boron compound in which the aromatic ring or the alkenyl group is bonded to the boron, the palladium (0) complex, the phosphine ligand and the base are used in not less than an equivalent amount with respect to X—$CH_2F$.

31. The method of producing a PET tracer according to claim 28, wherein the phosphine ligand is three times the palladium (0) complex in a mole ratio.

32. The method of producing a PET tracer according to claim 19, wherein the phosphine ligand is tri-o-tolylphosphine, the palladium (0) complex is tris(dibenzylideneacetone)dipalladium (0), X—$CH_2F$ is $CH_2^{18}FI$, and the $CH_2^{18}FI$ and said organic boron compound are reacted with each other.

33. The method of producing a PET tracer according to claim 32, wherein the base is potassium carbonate.

34. The method of producing a PET tracer according to claim 19, wherein said organic boron compound in which the aromatic ring or the alkenyl group is bonded to the boron is an aromatic boronic acid ester or an alkenyl boronic acid ester.

35. The method of producing a PET tracer according to claim 19, wherein the base is a carbonate or a phosphate.

36. The method of producing a PET tracer according to claim 19, wherein the aromatic ring includes a heterocycle.

* * * * *